United States Patent
Old et al.

(10) Patent No.: US 6,734,206 B1
(45) Date of Patent: May 11, 2004

(54) 3-OXA-8-AZAPROSTAGLANDIN ANALOGS AS AGENTS FOR LOWERING INTRAOCULAR PRESSURE

(75) Inventors: David W. Old, Irvine, CA (US); Thang D. Dinh, Garden Grove, CA (US); Robert M. Burk, Laguna Beach, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 10/453,207

(22) Filed: Jun. 2, 2003

(51) Int. Cl.[7] .................. A61K 31/4015; C07D 207/08
(52) U.S. Cl. .................. 514/424; 514/91; 514/343; 514/381; 514/422; 546/278.4; 548/413; 548/517; 548/525; 548/527; 548/550; 548/551
(58) Field of Search .................. 546/278.4; 548/517, 548/525, 527, 550, 551; 514/343, 381, 422, 424

(56) References Cited

U.S. PATENT DOCUMENTS

| | | | |
|---|---|---|---|
| 4,994,274 A | 2/1991 | Chan et al. | 424/427 |
| 5,028,624 A | 7/1991 | Chan et al. | 514/530 |
| 5,034,413 A | 7/1991 | Chan et al. | 514/530 |
| 5,446,041 A | 8/1995 | Chan et al. | 514/530 |
| 6,552,067 B2 * | 4/2003 | Cameron et al. | 514/424 |
| 6,642,266 B2 * | 11/2003 | Cameron et al. | 514/424 |
| 2003/0064964 A1 * | 4/2003 | Elworthy et al. | 514/91 |
| 2003/0149086 A1 * | 8/2003 | Cameron et al. | 514/365 |
| 2003/0176479 A1 * | 9/2003 | Cameron et al. | 514/381 |
| 2003/0207925 A1 * | 11/2003 | Cameron et al. | 514/365 |

FOREIGN PATENT DOCUMENTS

| | | |
|---|---|---|
| EP | 1 121 939 A2 | 8/2001 |
| JP | 2001-233792 | 8/2001 |
| WO | WO01/46140 A1 | 6/2001 |
| WO | WO 02/24647 A1 | 3/2002 |
| WO | WO 02/42268 A2 | 5/2002 |
| WO | WO 03/007941 A1 | 1/2003 |
| WO | WO-03/008377 * | 1/2003 |
| WO | 03/009872 A1 | 6/2003 |

OTHER PUBLICATIONS

Bito, L.Z., *Biological Protection with Prostaglandins*, Cohen, M.M., ed., Boca Raton, Fla, CRC Press Inc., 1985, pp. 231–252.

Bito, L.Z., *Applied Pharmacology in the Medical Treatment of Glaucomas*, Drance, S.M. and Neufeld, A.H. eds, New York, Grune & Stratton, 1984, pp. 477–505.

Nilsson et al, Invest. Ophthalmol. Vis. Sci. (suppl), 284 (1987).

Bito, L.Z., *Arch. Ophthalmol.* 105, 1036 (1987).

Siebold et al, *Prodrug* 5,3, 1989.

* cited by examiner

*Primary Examiner*—Fiona T. Powers
(74) *Attorney, Agent, or Firm*—Robert J. Baran; Martin A. Voet; Carlos A. Fisher

(57) ABSTRACT

The present invention provides a method of treating ocular hypertension or glaucoma which comprises administering to an animal having ocular hypertension or glaucoma therapeutically effective amount of a compound represented by the general formula I;

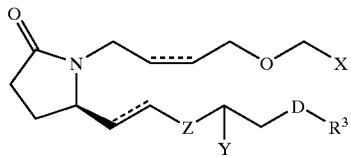

wherein X, Y, Z, D and $R^3$ are as defined in the specification.

21 Claims, No Drawings

3-OXA-8-AZAPROSTAGLANDIN ANALOGS AS AGENTS FOR LOWERING INTRAOCULAR PRESSURE

FIELD OF THE INVENTION

The present invention relates 3-oxa-8-azaprostaglandin analogues useful as potent ocular hypotensives that are particularly suited for the management of glaucoma.

BACKGROUND OF THE INVENTION

Description of Related Art

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupilary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical b-adrenoreceptor antagonists have traditionally been the drugs of choice for treating glaucoma.

Certain eicosanoids and their derivatives have been reported to possess ocular hypotensive activity, and have been recommended for use in glaucoma management. Eicosanoids and derivatives include numerous biologically important compounds such as prostaglandins and their derivatives. Prostaglandins can be described as derivatives of prostanoic acid which have the following structural formula:

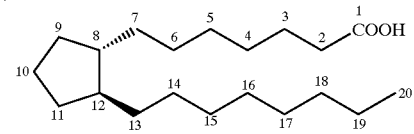

Various types of prostaglandins are known, depending on the structure and substituents carried on the alicyclic ring of the prostanoic acid skeleton. Further classification is based on the number of unsaturated bonds in the side chain indicated by numerical subscripts after the generic type of prostaglandin [e.g. prostaglandin $E_1$ ($PGE_1$), prostaglandin $E_2$ ($PGE_2$)], and on the configuration of the substituents on the alicyclic ring indicated by $\alpha$ or $\beta$ [e.g. prostaglandin $F_{2\alpha}$ ($PGF_{2\beta}$)].

Prostaglandins were earlier regarded as potent ocular hypertensives, however, evidence accumulated in the last decade shows that some prostaglandins are highly effective ocular hypotensive agents, and are ideally suited for the long-term medical management of glaucoma (see, for example, Bito, L. Z. *Biological Protection with Prostaglandins*, Cohen, M. M., ed., Boca Raton, Fla., CRC Press Inc., 1985, pp. 231–252; and Bito, L. Z., *Applied Pharmacology in the Medical Treatment of Glaucomas* Drance, S. M. and Neufeld, A. H. eds., New York, Grune & Stratton, 1984, pp. 477–505. Such prostaglandins include $PGF_{2\alpha}$, $PGF_{1\alpha}$, $PGE_2$, and certain lipid-soluble esters, such as $C_1$ to $C_2$ alkyl esters, e.g. 1-isopropyl ester, of such compounds.

Although the precise mechanism is not yet known experimental results indicate that the prostaglandin-induced reduction in intraocular pressure results from increased uveoscleral outflow [Nilsson et.al., *Invest. Ophthalmol. Vis. Sci.* (suppl), 284 (1987)].

The isopropyl ester of $PGF_{2\alpha}$ has been shown to have significantly greater hypotensive potency than the parent compound, presumably as a result of its more effective penetration through the cornea In 1987, this compound was described as "the most potent ocular hypotensive agent ever reported" [see, for example, Bito, L. Z., *Arch. Ophthalmol.* 105, 1036 (1987), and Siebold et.al., *Prodrug* 5 3 (1989)].

Whereas prostaglandins appear to be devoid of significant intraocular side effects, ocular surface (conjunctival) hyperemia and foreign-body sensation have been consistently associated with the topical ocular use of such compounds, in particular $PGF_{2\alpha}$ and its prodrugs, e.g., its 1-isopropyl ester, in humans. The clinical potentials of prostaglandins in the management of conditions associated with increased ocular pressure, e.g. glaucoma are greatly limited by these side effects.

In a series of co-pending United States patent applications assigned to Allergan, Inc. prostaglandin esters with increased ocular hypotensive activity accompanied with no or substantially reduced side-effects are disclosed. The co-pending U.S. Ser. No. 596,430 (filed 10 Oct. 1990, now U.S. Pat. No. 5,446,041), relates to certain 11-acyl-prostaglandins, such as 11-pivaloyl, 11-acetyl, 11-isobutyryl, 11-valeryl, and 11-isovaleryl $PGF_{2\alpha}$. Intraocular pressure reducing 15-acyl prostaglandins are disclosed in the co-pending application U.S. Ser. No. 175, 476 (filed 29 Dec. 1993). Similarly, 11,15- 9,15 and 9,11-diesters of prostaglandins, for example 11,15-dipivaloyl $PGF_{2\alpha}$ are known to have ocular hypotensive activity. See the co-pending patent applications U.S. Ser. No. 385,645 (filed 07 Jul. 1989, now U.S. Pat. No. 4,994,274), U.S. Ser. No. 584,370 (filed 18 Sep. 1990, now U.S. Pat. No. 5,028,624) and U.S. Ser. No. 585,284 (filed 18 Sep. 1990, now U.S. Pat. No. 5,034,413). The disclosures of all of these patent applications are hereby expressly incorporated by reference.

8-Azaprostaglandin analogs are disclosed in PCT Patent Application WO 01/46140 A1, WO 02/042268A2, WO 02/24647 A1, WO 03/00794 A1, EP 1 121 939 A2 and Japanese Patent 2001-233792

SUMMARY OF THE INVENTION

The present invention concerns a method of treating ocular hypertension which comprises administering to a mammal having ocular hypertension a therapeutically effective amount of a compound of formula I

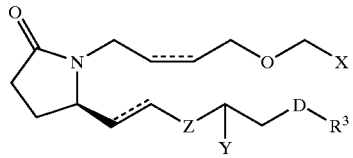

wherein hatched lines represent the α configuration, a triangle represents the β configuration, a wavy line represents either the α configuration or the β configuration and a dotted line represents the presence or absence of a double bond;

D represents a covalent bond or $CH_2$, O, S or NH;

X is $CO_2R$, $CONR_2$, $CH_2OR$, $P(O)(OR)_2$, $CONRSO_2R$, $SONR_2$ or

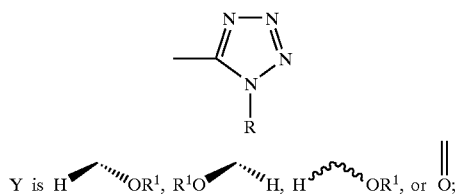

Y is H ⃫OR¹, R¹O⃫H, H⃫OR¹, or O;

Z is $CH_2$ or a covalent bond;

R is H or $R^2$;

$R^1$ is H, $R^2$, phenyl, or $COR^2$;

$R^2$ is $C_1$–$C_5$ lower alkyl or alkenyl and $R^3$ is selected from the group consisting of $R^2$, phenyl, thienyl, furanyl, pyridyl, benzothienyl, benzofuranyl, naphthyl, or substituted derivatives thereof, wherein the substituents maybe selected from the group consisting of $C_1$–$C_5$ alkyl, halogen, $CF_3$, CN, $NO_2$, $NR_2$, $CO_2R$ and OR.

In a still further aspect, the present invention relates to a pharmaceutical product, comprising a container adapted to dispense its contents in a metered form; and an ophthalmic solution therein, as hereinabove defined.

Finally, certain of the compounds represented by the above formula, disclosed below and utilized in the method of the present invention are novel and unobvious.

DETAILED DESCRIPTION OF THE INVENTION

The present invention relates to the use of 8-Azaprostaglandin analogs as ocular hypotensives. The compounds used in accordance with the present invention are encompassed by the following structural formula I:

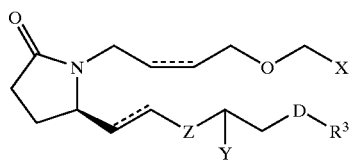

The preferred group of the compounds of the present invention includes compounds that have the following structural formula II.

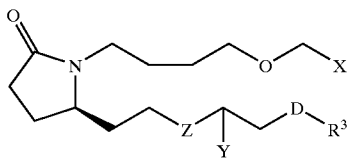

In the above formulae, the substituents and symbols are as hereinabove defined.

In the above formulae:

Preferably D represents a covalent bond or is $CH_2$; more preferably D is $CH_2$.

Preferably Z represents a covalent bond.

Preferably R is H or $C_1$–$C_5$ lower alkyl.

Preferably $R^1$ is H.

Preferably $R^3$ is selected from the group consisting of phenyl and monosubstituted derivatives thereof, e.g. chloro and trifluoromethyl phenyl, i.e. m-chlorophenyl.

Preferably X is $CO_2R$ and more preferably R is selected from the group consisting of H and methyl.

The above compounds of the present invention may be prepared by methods that are known in the art or according to the working examples below. The compounds, below, are especially preferred representative, of the compounds of the present invention.

(4-{(R)-2-[(E)-4-(3-chlorophenyl)-3-oxo-but-1-enyl]-5-oxo-pyrrolidin-1-yl}-butoxy)-acetic acid methyl ester (4-{(R)-2-[(E)-4-(3-Chlorophenyl)-3-oxo-but-1-enyl]-5-oxo-pyrrolidin-1-yl}-butoxy)-acetic acid (4-{(R)-2-[4-(3-Chlorophenyl)-3-oxo-butyl]-5-oxo-pyrrolidin-1-yl}-butoxy)-acetic acid methyl ester (4-{(R)-2-[4-(3-Chlorophenyl)-3-oxo-butyl]-5-oxo-pyrrolidin-1-yl}-butoxy)-acetic acid (4-{(R)-2-[4-(3-Chlorophenyl)-3-hydroxy-butyl]-5-oxo-pyrrolidin-1-yl}-butoxy)-acetic acid methyl ester (4-{(R)-2-[4-(3-Chlorophenyl)-3-hydroxy-butyl]-5-oxo-pyrrolidin-1-yl}-butoxy)-acetic acid (4-{(R)-2-[(E)-4-(3-Chlorophenyl)-3-hydroxy-but-1-enyl]-5-oxo-pyrrolidin-1-yl}-butoxy)-acetic acid methyl ester (4-{(R)-2-[(E)-4-(3-Chlorophenyl)-3-hydroxy-but-1-enyl]-5-oxo-pyrrolidin-1-yl}-butoxy)-acetic acid Pharmaceutical compositions may be prepared by combining a therapeutically effective amount of at least one compound according to the present invention, or a pharmaceutically acceptable acid addition salt thereof, as an active ingredient, with conventional ophthalmically acceptable pharmaceutical excipients, and by preparation of unit dosage forms suitable for topical ocular use. The therapeutically efficient amount typically is between about 0.0001 and about 5% (w/v), preferably about 0.001 to about 1.0% (w/v) in liquid formulations.

For ophthalmic application, preferably solutions are prepared using a physiological saline solution as a major vehicle. The pH of such ophthalmic solutions should preferably be maintained between 6.5 and 7.2 with an appropriate buffer system. The formulations may also contain conventional, pharmaceutically acceptable preservatives, stabilizers and surfactants.

Preferred preservatives that may be used in the pharmaceutical compositions of the present invention include, but are not limited to, benzalkonium chloride, chlorobutanol, thimerosal, phenylmercuric acetate and phenylmercuric nitrate. A preferred surfactant is, for example, Tween 80. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. The preferred chelating agent is edentate disodium, although other chelating agents may also be used in place or in conjunction with it.

The ingredients are usually used in the following amounts:

| Ingredient | Amount (% w/v) |
| --- | --- |
| active ingredient | about 0.001–5 |
| preservative | 0–0.10 |
| vehicle | 0–40 |
| tonicity adjustor | 1–10 |
| buffer | 0.01–10 |
| pH adjustor | q.s. pH 4.5–7.5 |
| antioxidant | as needed |
| surfactant | as needed |
| purified water | as needed to make 100% |

The actual dose of the active compounds of the present invention depends on the specific compound, and on the condition to be treated; the selection of the appropriate dose is well within the knowledge of the skilled artisan.

The ophthalmic formulations of the present invention are conveniently packaged in forms suitable for metered application, such as in containers equipped with a dropper, to facilitate the application to the eye. Containers suitable for dropwise application are usually made of suitable inert, non-toxic plastic material, and generally contain between about 0.5 and about 15 ml solution.

This invention is further illustrated by the following non-limiting Examples.

EXAMPLE 1

(4-{(R)-2-[(E)-4-(3-chlorolphenyl)-3-oxo-but-1-enyl]-5-oxo-pyrrolidin-1-yl}-butoxy)-acetic Acid Methyl Ester Sodium hydride (29 mg, 60% dispersion in oil, 0.73 mmol) was added to a solution of [3-(3-chlorophenyl)-2-oxopropyl]-phosphonic acid dimethyl ester (180 mg, 0.65 mmol) in THF (5 mL) at 0° C. The mixture was aged at rt for 40 min then recooled to 0° C. A solution of [4-(R)-(2-formyl-5-oxo-pyrrolidin-1-yl)-butoxy]-acetic acid methyl ester (0.72 mmol, crude from Procedure 1) in THF (2 mL) was added via cannula. The reaction was allowed to warm to rt and aged for 20 h. Acetic acid and water (1:1, 20 mL) was then added and the mixture was extracted with EtOAc (3×20 mL). The combined organic phase was washed with saturated aqueous $NaHCO_3$ (3×15 mL) and brine (30 mL) then dried ($Na_2SO_4$), filtered and concentrated in vacuo. The residue was purified by flash column chromatography (0%→2% MeOH/$CH_2Cl_2$) and then by preparative thin layer chromatography (5% MeOH/$CH_2Cl_2$) to afford 106 mg (40%) of (4-{(R)-2-[(E)-4-(3-chlorophenyl)-3-oxo-but-1-enyl]-5-oxo-pyrrolidin-1-yl}-butoxy)-acetic acid methyl ester.

EXAMPLE 2

4-{(R)-2-[(E)-4-(3-Chlorophenyl)-3-oxo-but-1-enyl]-5-oxo-pyrrolidin-1-yl}-butoxy)-acetic Acid A mixture of (4-{(R)-2-[(E)-4-(3-chlorophenyl)-3-oxo-but-1-enyl]-5-oxo-pyrrolidin-1-yl}-butoxy)-acetic acid methyl ester (2.4 mg, 0.006 mmol), rabbit liver esterase (1 mg, 134 units/mg), pH 7.2 phosphate buffer (2.5 mL) and acetonitrile (0.1 mL) was stirred together at rt for 18 h. Acetonitrile (5 mL) was then added and the mixture was concentrated in vacuo to dryness. The residue was purified by flash column chromatography (0%→10% MeOH/$CH_2Cl_2$) to afford 1.1 mg (47%) of (4-{(R)-2-[(E)-4-(3-chlorophenyl)-3-oxo-but-1-enyl]-5-oxo-pyrrolidin-1-yl}-butoxy)-acetic acid.

EXAMPLE 3

(4-{(R)-2-[4-(3-Chlorophenyl)-3-oxo-butyl]-5-oxo-pyrrolidin-1-yl}-butoxy)-acetic Acid Methyl Ester Pd/C (6 mg, 10 wt %) was added to a solution of (4-{(R)-2-[(E)-4-(3-chlorophenyl)-3-oxo-but-1-enyl]-5-oxo-pyrrolidin-1-yl}-butoxy)-acetic acid methyl ester (59 mg, 0.14 mmol) in methanol (2 mL). The reaction mixture was evacuated and refilled with hydrogen (3×) then stirred at rt under a balloon of hydrogen for 3.5 h. The reaction mixture was filtered through celite, washing with methanol (5 mL). The filtrate was concentrated in vacuo to afford 59 mg (99%) of (4-{(R)-2-[4-(3-Chlorophenyl)-3-oxo-butyl]-5-oxo-pyrrolidin-1-yl}-butoxy)-acetic acid methyl ester.

EXAMPLE 4

(4-{(R)-2-[4-(3-Chlorophenyl)-3-oxo-butyl]-5-oxo-pyrrolidin-1-yl}-butoxy)-acetic Acid A mixture of (4-{(R)-2-[4-(3-chlorophenyl)-3-oxo-butyl]-5-oxo-pyrrolidin-1-yl}-butoxy)-acetic acid methyl ester (8.1 mg, 0.02 mmol), rabbit liver esterase (1 mg, 134 units/mg), pH 7.2 phosphate buffer (3 mL) and acetonitrile (0.1 mL) was stirred together at rt for 16.5 h. Aqueous HCl (0.5 M, 5 mL) was added and the mixture was extracted with $CH_2Cl_2$ (3×5 mL). The combined organic phase was dried ($Na_2SO_4$), filtered and concentrated in vacuo to afford 1.6 mg (20%) of (4-{(R)-2-[(E)-4-(3-chlorophenyl)-3-oxo-but-1-enyl]-5-oxo-pyrrolidin-1-yl}-butoxy)-acetic acid.

EXAMPLE 5

(4-{(R)-2-[4-(3-Chlorophenyl)-3-hydroxy-butyl]-5-oxo-pyrrolidin-1-yl}-butoxy)-acetic Acid Methyl Ester Sodium borohydride (4.1 mg, 0.11 mmol) was added to a solution of (4{(R)-2-[4-(3-Chlorophenyl)-3-oxo-butyl]-5-oxo-pyrrolidin-1-yl}-butoxy)-acetic acid methyl ester (44 mg, 0.11 mmol) in $CH_2Cl_2$ (1 mL) at rt. Methanol (3 drops) was added and the reaction was stirred at rt for 4.5 h.

Aqueous HCl (0.5 M, 5 mL) was added and the mixture was extracted with CH$_2$Cl$_2$ (2×8 mL). The combined organic phase was dried (Na$_2$SO$_4$), filtered and concentrated in vacuo. The residue was purified by flash column chromatography (0%→3% MeOH/CH$_2$Cl$_2$) to afford 9.1 mg (21%) of (4-{(R)-2-[4-(3-chlorophenyl)-3-hydroxy-butyl]-5-oxo-pyrrolidin-1-yl}-butoxy)-acetic acid methyl ester.

EXAMPLE 6

(4-{(R)-2-[4-(3-Chlorophenyl)-3-hydroxy-butyl]-5-oxo-pyrrolidin-1-yl}-butoxy)-acetic Acid Aqueous lithium hydroxide (1.0 N, 0.04 mL) was added to a solution of (4-{(R)-2-[4-(3-chlorophenyl)-3-hydroxy-butyl]-5-oxo-pyrrolidin-1-yl}-butoxy)-acetic acid methyl ester (15 mg, 0.036 mmol) in THF (0.5 mL) at rt. After 1 h, aqueous HCl (1.0 N, 3 mL) was added and the mixture was extracted with CH$_2$Cl$_2$ (3×5 mL). The combined organic phase was dried (Na$_2$SO$_4$), filtered and concentrated in vacuo. The residue was purified by flash column chromatography (0%→3% MeOH/CH$_2$Cl$_2$) to afford 6.3 mg (43%) of (4-{(R)-2-[4-(3-chlorophenyl)-3-hydroxy-butyl]-5-oxo-pyrrolidin-1-yl}-butoxy)-acetic acid.

EXAMPLE 7

(4-{(R)-2-[(E)-4-(3-Chlorophenyl)-3-hydroxy-but-1-enyl]-5-oxo-pyrrolidin-1-yl}-butoxy)-acetic Acid Methyl Ester Sodium borohydride (4.3 mg, 0.11 mmol) was added to a solution of (4-{(R)-2-[(E)-4-(3-chlorophenyl)-3-oxo-but-1-enyl]-5-oxo-pyrrolidin-1-yl}-butoxy)-acetic acid methyl ester (42 mg, 0.10 mmol) in CH$_2$Cl$_2$ (1 mL) at 0° C. Methanol (3 drops) was added and the reaction was stirred at rt for 3 h. Aqueous HCl (0.5 M, 5 mL) was added and the mixture was extracted with CH$_2$Cl$_2$ (3×5 mL). The combined organic phase was dried (Na$_2$SO$_4$), filtered and concentrated in vacuo. The residue was purified by flash column chromatography (0%→5% MeOH/CH$_2$Cl$_2$) to afford 31 mg (73%) of (4-{(R)-2-[(E)-4-(3-chlorophenyl)-3-hydroxy-but-1-enyl]-5-oxo-pyrrolidin-1-yl}-butoxy)-acetic acid methyl ester.

EXAMPLE 8

(4-{(R)-2-[(E)-4-(3-Chlorolphenyl)-3-hydroxy-but-1-enyl]-5-oxo-pyrrolidin-1-yl}-butoxy)-acetic Acid Aqueous lithium hydroxide (1.0 N, 0.04 mL) was added to a solution of (4-{(R)-2-[(E)-4-(3-chlorophenyl)-3-hydroxy-but-1-enyl]-5-oxo-pyrrolidin-1-yl}-butoxy)-acetic acid methyl ester (16 mg, 0.039 mmol) in THF (0.25 mL) at rt. After 1 h, aqueous HCl (0.5 N, 3 mL) was added and the mixture was extracted with ETOAc (2×5 mL). The combined organic phase was washed with brine (10 mL), dried (Na$_2$SO$_4$), filtered and concentrated in vacuo to afford 15 mg (97%) of (4-{(R)-2-[(E)-4-(3-chlorophenyl)-3-hydroxy-but-1-enyl]-5-oxo-pyrrolidin-1-yl}-butoxy)-acetic acid.

Procedure 1

[4-(R)-(2-Formyl-5-oxo-pyrrolidin-1-yl)-butoxy]-acetic Acid Methyl Ester

Step 1. (4-Hydroxy-butoxy)-acetic Acid Methyl Ester.

Sodium hydride (4.44 g, 60% dispersion in oil, 111 mmol) was added to a solution of 1,4-butanediol (10.0 g, 111 mmol) in THF (200 mL). After stirring 1 h at rt, the mixture was cooled to 0° C. and methyl bromomethylacetate (10.82 mL, 114 mmol) was added and the reaction was allowed to warm to room temperature. After 16 h, water (100 mL) was added and the mixture was extracted with EtOAc (3×100 mL). The combined organic phase was washed with brine (2×100 mL), dried (Na$_2$SO$_4$), filtered and concentrated in vacuo. The residue was purified by flash column chromatography (20%→30% EtOAc/Hexane) to afford 2.88 g (16%) of (4-hydroxy-butoxy)-acetic acid methyl ester as a colorless oil.

Step 2. (4-Bromo-butoxy)-acetic Acid Methyl Ester.

Triphenylphosphine (5.59 g, 21.3 mmol), bromine (1.1 mL, 21.5 mmol) and imidazole (1.41 g, 20.7 mmol) were sequentially added to a solution of (4-hydroxy-butoxy)-acetic acid methyl ester (2.88 g, 17.8 mmol) in CH$_2$Cl$_2$ (15 mL) at 0° C. under nitrogen. After 1 h, the mixture was filtered through basic alumina, rinsing with 5% EtOAc/Hexane (40 mL). The filtrate was concentrated and the residue was purified by flash column chromatography (0%→20% EtOAc/Hexane) to afford 2.02 g (51%) of (4-bromo-butoxy)-acetic acid methyl ester as a colorless oil.

Step 3. {4-[(R)-2-(tert-Butyldimethylsilanyloxymethyl)-5-oxo-pyrrolidin-1-yl]-butoxy}-acetic Acid Methyl Ester.

Sodium hydride (192 mg, 60% dispersion in oil, 4.8 mmol) was added to a solution of 5-(tert-butyldimethylsilanyloxymethyl)-pyrrolidin-2-one (1.0 g, 4.4 mmol) in DMF (8 mL). After stirring for 1 h at rt, a solution of (4-bromo-butoxy)-acetic acid methyl ester (1.08 g, 4.8 mmol) in DMF (4 mL) was added. The resulting mixture was heated at 90° C. for 18 h. The reaction was cooled to rt then water (75 mL) was added and the mixture was extracted with EtOAc (3×50 mL). The combined organic phase was washed with brine (100 mL), dried (Na$_2$SO$_4$), filtered and concentrated in vacuo. The residue was purified by flash column chromatography (0%→20% EtOAc/CH$_2$Cl$_2$) to afford 758 mg of a mixture of starting material and {4-[(R)-2-(tert-butyldimethylsilanyloxymethyl)-5-oxo-pyrrolidin-1-yl]-butoxy}-acetic acid methyl ester, which was taken on in the next step without further purification.

Step 4. [4-(R)-2-Hydroxymethyl-5-oxo-pyrrolidin-1-yl)-butoxy]-acetic Acid Methyl Ester.

Tetrabutylammonium fluoride (3.0 mL, 1.0 M in THF, 3.0 mmol) was added to a solution of impure {4-[(R)-2-(tert-butyldimethylsilanyloxymethyl)-5-oxo-pyrrolidin-1-yl]-butoxy}-acetic acid methyl ester (758 mg, ~1.98 mmol) in THF (3 mL) at 0° C. under nitrogen. The reaction was allowed to warm to rt and was aged for 18 h. THF was removed in vacuo, saturated aqueous NaHCO$_3$ (50 mL) was added and the mixture was extracted with CHCl$_3$ (2×30 mL). The combined organic phase was dried (Na$_2$SO$_4$), filtered and concentrated in vacuo. The residue was purified by flash column chromatography (0%→3% MeOH/CH$_2$Cl$_2$) to afford 188 mg (17% over two steps) of [4-(R)-2-hydroxymethyl-5-oxo-pyrrolidin-1-yl)-butoxy]-acetic acid methyl ester.

Step 5. [4-(R)-(2-Formyl-5-oxo-pyrrolidin-1-yl)-butoxy]-acetic Acid Methyl Ester.

1-(3-Dimethylaminopropyl)-3-ethylcarbodiimide hydrochloride (412 mg, 2.15 mmol) and DMSO (0.20 mL, 2.82 mmol) were added to a solution of [4-(R)-2-hydroxymethyl-5-oxo-pyrrolidin-1-yl)-butoxy]-acetic acid methyl ester (185 mg, 0.72 mmol) in benzene (5 mL). The mixture was cooled to 0° C. then pyridinium trifluoroacetate (153 mg, 0.79 mmol) was added. The reaction was aged at 0° C. for 15 min, then at rt for 2 h. The solution was decanted from the oil and the oil residue was washed with benzene (3×4 mL). The combined benzene phase was concentrated in vacuo to afford the title compound which was used without further purification.

These compounds are tested for in vitro activity as described below and the results given in the Tables.

| Example Number | Structure | Binding Data (IC50 in nM) | | | Functional Data (EC50 in nM) | | | | | | | |
|---|---|---|---|---|---|---|---|---|---|---|---|---|
| | | hEP2 | hEP3D | hEP4 | hFP | hEP1 | hEP2 | hEP3A | hEP4 | hTP | hIP | hDP |
| 1 | 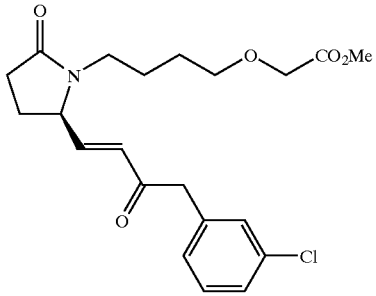 | NT | NT | NT | NA | 721 | NA | NA | 61 | NA | NA | NT |
| 2 | 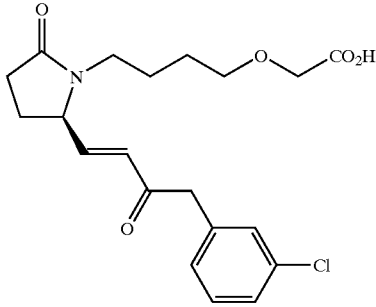 | NA | NT | >10000 | NA | NA | NA | >10000 | NA | <10000 | NA | NT |
| 3 | 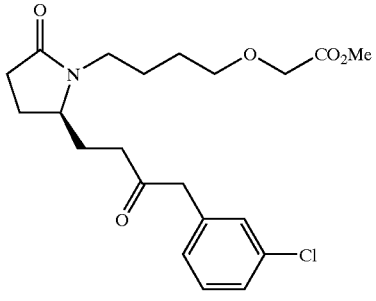 | NT | NT | NT | NA | NA | NA | NA | >10000 | >10000 | NA | NT |
| 4 | 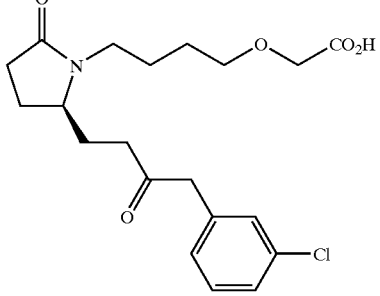 | NA | NT | 3100 | NA | NA | NA | NA | 1722 | >10000 | NA | NT |

-continued

| Example Number | Structure | Binding Data (IC50 in nM) | | | Functional Data (EC50 in nM) | | | | | | | |
|---|---|---|---|---|---|---|---|---|---|---|---|---|
| | | hEP2 | hEP3D | hEP4 | hFP | hEP1 | hEP2 | hEP3A | hEP4 | hTP | hIP | hDP |
| 5 | 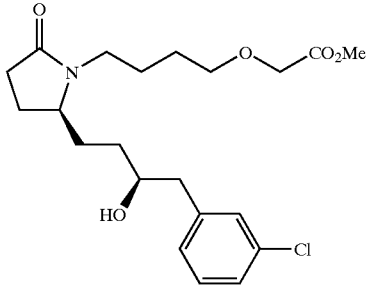 | NT | NT | NT | NA | >10000 | NA | NA | 1778 | NA | NA | NT |
| 6 | 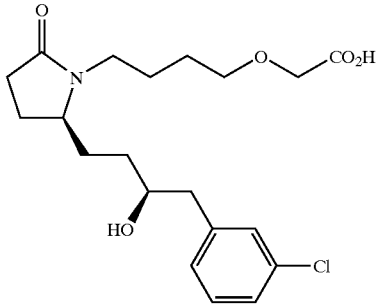 | NA | NT | 562 | NA | 3808 | NA | NA | 192 | >10000 | NA | NT |
| 7 | 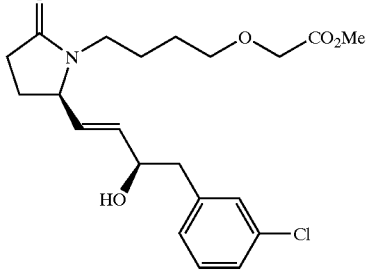 | NT | NT | NT | NA | NA | NA | NA | <10000 | NA | NA | NT |
| 8 | 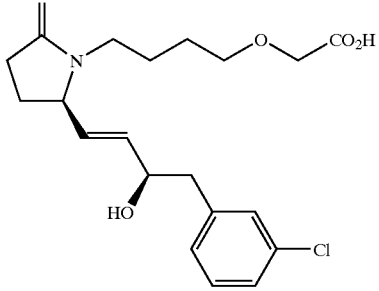 | NA | NA | 30 | NA | NA | NA | NA | 11 | >10000 | NA | NT |

NA = not active
NT = not tested

Human Recombinant EP$_1$, EP$_2$, EP$_3$, EP$_4$, FP, TP, IP and DP Receptors: Stable Transfectants Plasmids encoding the human EP$_1$, EP$_2$, EP$_3$, EP$_4$, FP, TP, IP and DP receptors were prepared by cloning the respective coding sequences into the eukaryotic expression vector pCEP4 (Invitrogen). The pCEP4 vector contains an Epstein Barr virus (EBV) origin of replication, which permits episomal replication in primate cell lines expressing EBV nuclear antigen (EBNA-1). It also contains a hygromycin resistance gene that is used for eukaryotic selection. The cells employed for stable transfection were human embryonic kidney cells (HEK-293) that were transfected with and express the EBNA-1 protein. These HEK-293-EBNA cells (Invitrogen) were grown in medium containing Geneticin (G418) to maintain expression of the EBNA-1 protein. HEK-293 cells were grown in DMEM with 10% fetal bovine serum (FBS), 250 μg ml$^{-1}$ G418 (Life Technologies)

and 200 μg ml$^{-1}$ gentamicin or penicillin/streptomycin. Selection of stable transfectants was achieved with 200 μg ml$^{-1}$ hygromycin, the optimal concentration being determined by previous hygromycin kill curve studies.

For transfection, the cells were grown to 50–60% confluency on 10 cm plates. The plasmid pCEP4 incorporating cDNA inserts for the respective human prostanoid receptor (20 μg) was added to 500 μl of 250 mM CaCl$_2$. HEPES buffered saline×2 (2×HBS, 280 mM NaCl, 20 mM HEPES acid, 1.5 mM Na$_2$HPO$_4$, pH 7.05–7.12) was then added dropwise to a total of 500 μl, with continuous vortexing at room temperature. After 30 min, 9 ml DMEM were added to the mixture. The DNA/DMEM/calcium phosphate mixture was then added to the cells, which had been previously rinsed with 10 ml PBS. The cells were then incubated for 5 hr at 37° C. in humidified 95% air/5% CO$_2$. The calcium phosphate solution was then removed and the cells were treated with 10% glycerol in DMEM for 2 min. The glycerol solution was then replaced by DMEM with 10% FBS. The cells were incubated overnight and the medium was replaced by DMEM/10% FBS containing 250 μg ml$^{-1}$ G418 and penicillin/streptomycin. The following day hygromycin B was added to a final concentration of 200 μg ml$^{-1}$.

Ten days after transfection, hygromycin B resistant clones were individually selected and transferred to a separate well on a 24 well plate. At confluence each clone was transferred to one well of a 6 well plate, and then expanded in a 10 cm dish. Cells were maintained under continuous hygromycin selection until use.

Radioligand Binding

Radioligand binding studies on plasma membrane fractions prepared for cells stably transfected with the cat or human receptor were performed as follows. Cells washed with TME buffer were scraped from the bottom of the flasks and homogenized for 30 sec using a Brinkman PT 10/35 polytron. TME buffer was added as necessary to achieve a 40 ml volume in the centrifuge tubes. TME is comprised of 50 mM TRIS base, 10 mM MgCl$_2$, 1 mM EDTA; pH 7.4 is achieved by adding 1 N HCl. The cell homogenate was centrifuged at 19,000 rpm for 20–25 min at 4° C. using a Beckman Ti-60 or Tt-70 rotor. The pellet was then resuspended in TME buffer to provide a final protein concentration of 1 mg/ml, as determined by Bio-Rad assay. Radioligand binding assays were performed in a 100 μl or 200 μl volume.

The binding of [$^3$H](N) PGE$_2$ (specific activity 165 Ci/mmol) was determined in duplicate and in at least 3 separate experiments. Incubations were for 60 min at 25° C. and were terminated by the addition of 4 ml of ice-cold 50 mM TRIS-HCl followed by rapid filtration through Whatman GF/B filters and three additional 4 ml washes in a cell harvester (Brandel). Competition studies were performed using a final concentration of 2.5 or 5 nM [$^3$H](N) PGE$_2$ and non-specific binding was determined with 10$^{-5}$ M unlabelled PGE$_2$.

For radioligand binding on the transient transfectants, plasma membrane fraction preparation was as follows. COS-7 cells were washed with TME buffer, scraped from the bottom of the flasks, and homogenized for 30 sec using a Brinkman PT 10/35 polytron. TME buffer was added to achieve a final 40 ml volume in the centrifuge tubes. The composition of TME is 100 mM TRIS base, 20 mM MgCl$_2$, 2M EDTA; 10N HCl is added to achieve a pH of 7.4.

The cell homogenate was centrifuged at 19000 rpm for 20 min at 4° C. using a Beckman Ti-60 rotor. The resultant pellet was resuspended in TME buffer to give a final 1 mg/ml protein concentration, as determined by Biorad assay. Radioligand binding assays were performed in a 200 μl volume.

The binding of [$^3$H] PGE$_2$ (specific activity 165 Ci or mmol$^{-1}$) at EP$_{3D}$, receptors and [$^3$H]-SQ29548 (specific activity 41.5 Ci mmol$^{-1}$) at TP receptors were determined in duplicate in at least three separate experiments. Radiolabeled PGE$_2$ was purchased from Amersham, radiolabeled SQ29548 was purchased from New England Nuclear. Incubations were for 60 min at 25° C. and were terminated by the addition of 4 ml of ice-cold 50 mM TRIS-HCl, followed by rapid filtration through Whatman GF/B filters and three additional 4 ml washes in a cell harvester (Brandel). Competition studies were performed using a final concentration of 2.5 or 5 nM [$^3$H]-PGE$_2$, or 10 nM [$^3$H]-SQ 29548 and non-specific binding determined with 10 μM of the respective unlabeled prostanoid. For all radioligand binding studies, the criteria for inclusion were >50% specific binding and between 500 and 1000 displaceable counts or better.

The effects of the compounds of this invention on intraocular pressure may be measured as follows. The compounds are prepared at the desired concentrations in a vehicle comprising 0.1% polysorbate 80 and 10 mM TRIS base. Dogs are treated by administering 25 μl to the ocular surface, the contralateral eye receives vehicle as a control. Intraocular pressure is measured by applanation pneumatonometry. A topical once daily dosing of (4-{(R)-2-[(E)-4-(3-chlorophenyl)-3-hydroxy-but-1-enyl]-5-oxo-pyrrolidin-1-yl}-butoxy)-acetic acid [example 8] (0.1%) gave a maximum IOP decrease from baseline of 4.9 mmHg (26.6%) at 52 h in normotensive dogs (n=8). The maximum ocular surface hyperemia score was 1.5 (1.5 at 26, 50 and 52 h).

Certain of the compounds of this invention are useful in lowering elevated intraocular pressure in mammals, e.g. humans, and in treating other diseases and conditions which are responsive to prostaglandin analogues, e.g. glaucoma; cardiovascular; e.g. acute myocardial infarction, vascular thrombosis, hypertension, pulmonary hypertension, ischemic heart disease, congestive heart failure, and angina pectoris; pulmonary-respiratory; gastrointestinal; reproductive and allergic diseases; osteoporosis and shock.

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the overall scope hereof; rather, the ambit of the present invention is to be governed only by the lawful construction of the appended claims.

What is claimed is:

1. A method of treating ocular hypertension or glaucoma which comprises administering to an animal having ocular hypertension or glaucoma a therapeutically effective amount of a compound represented by the general formula I;

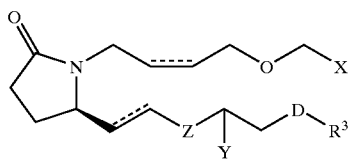

wherein hatched lines represent the α configuration, a triangle represents the β configuration, a wavy line represents either the α configuration or the β configuration and a dotted line represents the presence or absence of a double bond;

D represents a covalent bond or $CH_2$, O, S or NH;

X is $CO_2R$, $CONR_2$, $CH_2OR$, $P(O)(OR)_2$, $CONRSO_2R$, $SONR_2$ or

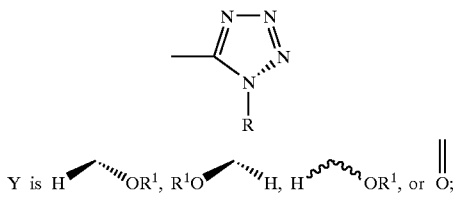

Y is $H^{\cdots}OR^1$, $R^1O^{\cdots}H$, $H^{\sim\sim}OR^1$, or O;

Z is $CH_2$ or a covalent bond;

R is H or $R^2$;

$R^1$ is H, $R^2$, phenyl, or $COR^2$;

$R^2$ is $C_1$–$C_5$ lower alkyl or alkenyl and $R^3$ is selected from the group consisting of $R^2$, phenyl, thienyl, furanyl, pyridyl, benzothienyl, benzofuranyl, naphthyl, or substituted derivatives thereof, wherein the substituents maybe selected from the group consisting of $C_1$–$C_5$ alkyl, halogen, $CF_3$, CN, $NO_2$, $NR_2$, $CO_2R$ and OR.

2. The method according to claim 1 wherein said compound is represented by the general formula II;

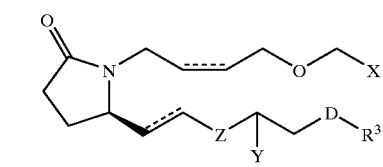

3. The method of claim 1 wherein Z represents a covalent bond.

4. The method of claim 1 wherein D is $CH_2$.

5. The method of claim 1 wherein X is $CO_2R$.

6. The method of claim 5 wherein R is selected from the group consisting of H and ethyl.

7. The method of claim 5 wherein R is H, or $C_1$–$C_5$ alkyl.

8. The method of claim 1 wherein $R^1$ is H.

9. The method of claim 1 wherein $R^3$ is selected from the group consisting of phenyl, chlorophenyl and trifluoromethylphenyl.

10. The method of claim 1 wherein said compound is selected from the group consisting of (4-{(R)-2-[4-(3-Chlorophenyl)-3-hydroxy-butyl]-5-oxo-pyrrolidin-1-yl}-butoxy)-acetic acid and (4-{(R)-2-[(E)-4-(3-Chlorophenyl)-3-hydroxy-but-1-enyl]-5-oxo-pyrrolidin-1-yl}-butoxy)-acetic acid.

11. An ophthalmic solution comprising a therapeutically effective amount of a compound represented by the general Formula I

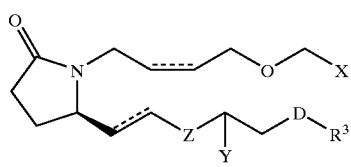

wherein hatched lines represent the α configuration, a triangle represents the β configuration, a wavy line represents the α configuration or the β configuration and a dotted line represents the presence or absence of a double bond;

D represents a covalent bond or $CH_2$, O, S or NH;

X is $CO_2R$, $CONR_2$, $CH_2OR$, $P(O)(OR)_2$, $CONRSO_2R$, $SONR_2$ or

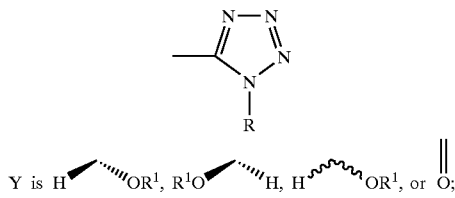

Y is $H^{\cdots}OR^1$, $R^1O^{\cdots}H$, $H^{\sim\sim}OR^1$, or O;

Z is $CH_2$ or a covalent bond;

R is H or $R^2$;

$R^1$ is H, $R^2$, phenyl, or $COR^2$;

$R^2$ is $C_1$–$C_5$ lower alkyl or alkenyl and $R^3$ is selected from the group consisting of $R^2$, phenyl, thienyl, furanyl, pyridyl, benzothienyl, benzofuranyl, naphthyl or substituted derivatives thereof, wherein the substituents maybe selected from the group consisting of $C_1$–$C_5$ alkyl, halogen, $CF_3$, CN, $NO_2$, $NR_2$, $CO_2R$ and OR in admixture with a non-toxic, ophthalmically acceptable liquid vehicle, packaged in a container suitable for metered application.

12. A pharmaceutical product, comprising a container adapted to dispense the contents of said container in metered form; and an ophthalmic solution according to claim 11 in said container.

13. A compound useful for treating ocular hypertension or glaucoma which comprises a compound represented by the general formula I;

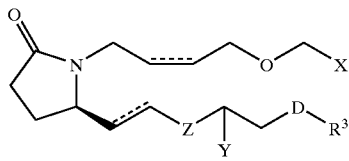

wherein hatched lines represent the α configuration, a triangle represents the β configuration, a wavy line represents either the α configuration or the β configuration and a dotted line represents the presence or absence of a double bond;

D represents a covalent bond or $CH_2$, O, S or NH;

X is $CONR_2$, $CH_2OR$, $P(O)(OR)_2$, $CONRSO_2R$ or $SONR_2$;

Y is $H^{\cdots}OR^1$, $R^1O^{\cdots}H$, $H^{\sim\sim}OR^1$, or O;

Z is $CH_2$ or a covalent bond;

R is H or $R^2$;

$R^1$ is H, $R^2$, phenyl, or $COR^2$;

$R^2$ is $C_1$–$C_5$ lower alkyl or alkenyl and $R^3$ is selected from the group consisting of $R^2$, phenyl, thienyl, furanyl, pyridyl, benzothienyl, benzofuranyl, naphthyl, or substituted derivatives thereof, wherein the substituents maybe selected from the group consisting of $C_1$–$C_5$ alkyl, halogen, $CF_3$, CN, $NO_2$, $NR_2$, $CO_2R$ and OR.

14. The method according to claim 1 wherein said compound is represented by the general formula II;

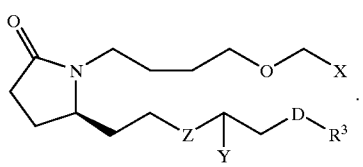

15. The method of claim 14 wherein Z represents a covalent bond.

16. The method of claim 14 wherein D is $CH_2$.

17. The method of claim 14 wherein X is $CO_2 R$.

18. The method of claim 17 wherein R is selected from the group consisting of H and ethyl.

19. The method of claim 17 wherein R is H, or $C_1$–$C_5$ alkyl.

20. The method of claim 14 wherein $R^1$ is H.

21. The method of claim 14 wherein $R^3$ is selected from the group consisting of phenyl, chlorophenyl and trifluoromethylphenyl.

* * * * *

UNITED STATES PATENT AND TRADEMARK OFFICE
CERTIFICATE OF CORRECTION

PATENT NO. : 6,734,206 B1
DATED : May 11, 2004
INVENTOR(S) : Old et al.

It is certified that error appears in the above-identified patent and that said Letters Patent is hereby corrected as shown below:

Column 2,
Line 33, delete "cornea" and insert in place thereof -- cornea. --

Column 3,
Line 1, delete "WO 03/00794" and insert in place thereof -- WO 03/007941 --

Column 5,
Line 66, delete "(0.72" insert in place thereof -- ( ~ 0.72 --

Column 11,
Figure 5, delete the formula and insert in place thereof

-- 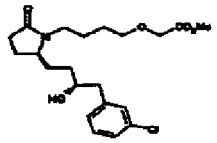 --

Figure 6, delete the formula and insert in place thereof

-- 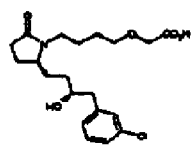 --

Figure 7, delete formula and insert in place thereof

-- 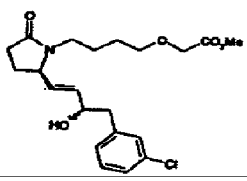 --

UNITED STATES PATENT AND TRADEMARK OFFICE
CERTIFICATE OF CORRECTION

PATENT NO.    : 6,734,206 B1
DATED         : May 11, 2004
INVENTOR(S)   : Old et al.

It is certified that error appears in the above-identified patent and that said Letters Patent is hereby corrected as shown below:

Column 12,
Figure 8, delete formula and insert in place thereof

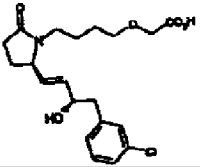

Signed and Sealed this

Thirtieth Day of November, 2004

JON W. DUDAS
*Director of the United States Patent and Trademark Office*